United States Patent [19]

Curran

[11] 4,011,331
[45] Mar. 8, 1977

[54] PIPERIDINE DERIVATIVES

[75] Inventor: Adrian Charles Ward Curran, Newcastle-upon-Tyne, England

[73] Assignee: John Wyeth & Brother Limited, Maidenhead, England

[22] Filed: Feb. 28, 1975

[21] Appl. No.: 554,258

[30] Foreign Application Priority Data

Mar. 5, 1974  United Kingdom ............... 9766/74

[52] U.S. Cl. ........................... 424/267; 260/293.73; 260/293.85; 260/293.87

[51] Int. Cl.² ...................................... C07D 295/14

[58] Field of Search ................ 260/293.85, 293.73; 424/267

[56] References Cited

UNITED STATES PATENTS 3,882,114  5/1975  Kalopissis et al. .......... 260/247.1 R Primary Examiner—G. Thomas Todd

[57] ABSTRACT

The invention relates to a compound of formula I

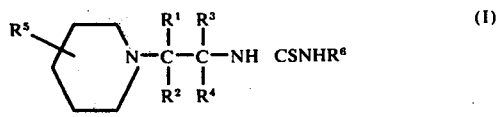

or pharmaceutically acceptable acid addition salts thereof, wherein $R^1$, $R^2$, $R^3$, $R^4$ and $R^5$ are the same or different and represent hydrogen, or lower alkyl, and $R^6$ represents hydrogen, alkyl or 1 to 3 carbon atoms, which may be substituted by diloweralkylamino; lower alkanoyl or aroyl.

The compounds are either anti-ulcer agents or intermediates for such compounds.

5 Claims, No Drawings

PIPERIDINE DERIVATIVES

The invention relates to piperidine derivatives to processes for preparing them and to pharmaceutical compositions containing them.

According to the invention there is provided compounds of formula I

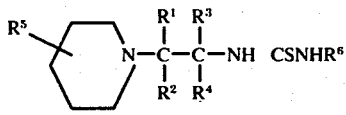 (I)

or pharmaceutically acceptable acid addition salts thereof, wherein $R^1$, $R^2$, $R^3$, $R^4$ and $R^5$ are the same of different and represent hydrogen, or lower alkyl, and $R^6$ represents hydrogen, alkyl of 1 to 3 carbon atoms, which may be substituted by diloweralkylamino; lower alkanoyl or aroyl.

When $R^1$, $R^2$, $R^3$, $R^4$ or $R^5$ is a lower alkyl radical it may be a straight or branched chain having from 1 to 6 carbon atoms, e.g. methyl, ethyl, n- and iso- propyl, and n, s and t-butyl.

$R^6$ is preferably hydrogen or methyl but may be ethyl or propyl. $R^1$, $R^2$, $R^3$ and $R^4$ are preferably hydrogen. When $R^6$ is aroyl it may be benzoyl or substituted benzoyl e.g. halo-benzoyl. When $R^6$ is lower alkanoyl it may have from 2 to 7 carbon atoms; examples are acetyl, propionyl, butyryl, pentanoyl and hexanoyl.

The compounds of formula I can form acid addition salts with inorganic acids e.g. hydrochloric, hydrobromic, sulphuric, or nitric acids, or organic acids e.g. citric, fumaric, maleic or tartaric acids. These acid addition salts are included in the invention.

Compounds of formula I, wherein $R^6$ is hydrogen or alkyl of 1 to 3 carbon atoms which may be substituted by diloweralkylamino; are anti-ulcer agents which possess one or more of the following pharmacological properties: anti-ulcer, anti-secretory or gastric anti-histamine activity. Anti-ulcer activity is determined by the method of Brodie and Hanson, J. Applied Physiology, 15, 291, 1960. Anti-secretory activity and gastric antihistamine activity are determined by the method of H. Shay, D. Sun and H. Greenstein, Gastroenterology 1954, 26, 906–13.

The other compounds of formula I are intermediates.

The invention includes processes for preparing the compounds of formula I.

A process for preparing compound of formula I, wherein $R^6$ is alkyl of 1 – 3 carbon atoms, which may be substituted by dialkylamino; lower alkanoyl or aroyl comprises reacting a compound of formula II

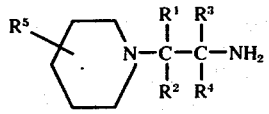 (II)

wherein $R^1$, $R^2$, $R^3$, $R^4$ and $R^5$ are as defined in connection with formula I, with an isothiocyanate of formula $R^6NCS$ wherein $R^6$ is as defined immediately above.

Compounds of formula I, wherein $R^6$ is hydrogen may be prepared by hydrolysing a compound of formula I wherein $R^6$ is lower alkanoyl or aroyl.

The hydrolysis may be carried out by treatment with a suitable base e.g. an alkali or alkaline earth metal hydroxide. Conveniently sodium or potassium hydroxide may be used.

The invention also includes pharmaceutical compositions comprising a compound of formula I wherein $R^6$ is hydrogen, or alkyl of 1 – 3 carbon atoms, which may be substituted by diloweralkylamino; and a pharmaceutical carrier.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be carried or adjusted from 5 mg. or less to 500 or more, according to the particular need and the activity of the active ingredient. The invention also includes the compounds in the absence of carrier where the compounds are in unit dosage form.

The anti-ulcer composition of the invention will be administered orally in either liquid or solid composition form. These compositions may include one or more antacid ingredients e.g. aluminium hydroxide, magnesium hydroxide or bismuth carbonate, aluminium glycinate, calcium carbonate magnesium trisilicate, sodium bicarbonate or the alumina gel described in British Pat. Specification No. 1,284,394.

The invention is illustrated by the following Examples:

EXAMPLE 1

N-Methyl-N'-(2-piperidinoethyl)thiourea

Methylisothiocyanate (0.73 g., 0.01 mol.) was added to a solution of 2-(N-piperidino)ethylamine (1.28 g., 0.01 mol) in chloroform (25 ml.) and dimethylformamide (2.5 ml.) and the mixture was heated at reflux for 2.5 hours with stirring. The solvent was removed in vacuo and the residue diluted with anhydrous ether and treated with an excess of an ethereal solution of hydrogen chloride. The resultant solid was filtered and recrystallised from isopropyl alcohol to give the title compound as the hdyrochloride colourless needles (0.9 g.) m.p. 166° C. (Found C, 45.7; H,8.6; N,17.2 $C_9H_{19}N_3S.HCl$ requires: C,45.5; H,8.5; N, 17.6%).

The product exhibits anti-ulcer, anti-secretory and gastric anti-histamine activity.

EXAMPLE 2

N-Methyl-N'[2-(3-piperidinopropyl)]thiourea 1-(2-Aminopropyl)piperidine, prepared according to the method described in C.A. 1959, 53, 18958e, is reacted with methylisothiocyanate, in the manner described in Example 1, to give the title compound.

EXAMPLE 3

N-Benzoyl-N'(2-piperidinoethyl)thiourea

By the general method described in Example 1, 2-(N-piperidino)ethylamine is reacted with benzoylisothiocyanate to give the title compound. Hydrolysis with 10% sodium hydroxide gives N-(2-piperidinoethyl)thiourea.

EXAMPLE 4

N-Acetyl-N'(2-piperidinoethyl)thiourea

By the general method described in Example 1, 2-(N-piperidino)ethylamine is reacted with acetylisothiocyanate to give the title compound. Hydrolysis with 10% sodium hydroxide gives N-(2-piperidinoethyl)thiourea.

EXAMPLE 5

N-Methyl-N'-[2-(1-piperidinobutyl]-thiourea

By the general method described in Example 1, 1-(2-aminobutyl)-piperidine is reacted with methyl isothiocyanate to give the title compound.

EXAMPLE 6

N-Methyl-N'-[2-(2 methyl-1-piperidino propyl]-thiourea

By the general method described in Example 1, 1-(2-aminoisobutyl)-piperidine is reacted with methyl isothiocyanate to give the title compound.

EXAMPLE 7

N-Methyl-N'-[1-(2-piperidinopropyl)]-thiourea

By the general method described in Example 1, 1-(2-aminoisopropyl)-piperidine is reacted with methyl isothiocyanate to give the title compound.

EXAMPLE 8

N-Methyl-N'-[2-(2,6-dimethylpiperidino)-ethyl]-thiourea

By the general method described in Example 1, 1-(2-aminoethyl)-2,6-dimethylpiperidine is reacted with methyl isothiocyanate to give the title compound.

EXAMPLE 9

N-Methyl-N'-[2-(2-ethylpiperidino)-ethyl]-thiourea

By the general method described in Example 1, 1-(2-aminoethyl)-2-ethylpiperidine is reacted with methyl isothiocyanate to give the title compound.

EXAMPLE 10

N-(2-Diethylaminoethyl)-N'-(2-piperidinoethyl)-thiourea

By the general method described in Example 1, 1-(2-aminoethyl)-piperidine is reacted with diethylaminoethyl isothiocyanate to give the title compound.

EXAMPLE 11

N-p-Chloro-benzoyl-N'(2-piperidinoethyl)thiourea

By the general method described in Example 1 2-(N-piperidino)ethylamine is reacted with p-chlorobenzoyl isothiocyanate to give the title compound. Hydrolysis with 10% sodium hydroxide gives N-(2-piperidinoethyl) thiourea.

EXAMPLE 12

N-Propionyl-N'[2-(2,6-dimethylpiperidino)-ethyl]thiourea

By the general method described in Example 1, 1-(2-aminoethyl)-2,6-dimethylpiperidine is reacted with propionyl isothiocyanate to give the title compound which may be hydrolysed with 10% sodium hydroxide to give N-2[(2,6-dimethylpiperidino)-ethyl]thiourea.

I claim:
1. A compound of formula I

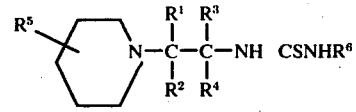

or pharmaceutically acceptable acid addition salts thereof, wherein $R^1$, $R^2$, $R^3$, $R^4$ and $R^5$ are the same or different and represent hydrogen, or lower alkyl, and $R^6$ represents hydrogen, alkyl of 1 to 3 carbon atoms, which may be substituted by diloweralkylamino; lower alkanoyl, benzoyl or halobenzoyl.

2. A compound as claimed in claim 1, which has the formula II

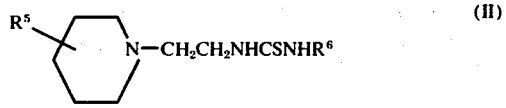

or a pharmaceutically acceptable acid addition salt thereof wherein $R^5$ and $R^6$ are as defined in claim 1.

3. A compound as claimed in claim 1, which is N-methyl-N'-(2-piperidinoethyl) thiourea or a pharmaceutically acceptable acid addition salt thereof.

4. A compound as claimed in claim 1, which is N-methyl-N'-(2-piperidinoethyl) thiourea hydrochloride.

5. A pharmaceutical composition comprising an anti-ulcer effective amount of a compound as claimed in claim 1, wherein $R^1$, $R^2$, $R^3$, $R^4$ and $R^5$ are as defined in claim 1 and $R^6$ is hydrogen or alkyl of 1 to 3 carbon atoms, which may be substituted by diloweralkylamino, and a pharmaceutically acceptable carrier.

* * * * *